United States Patent [19]

Okamoto et al.

[11] Patent Number: 5,776,357
[45] Date of Patent: Jul. 7, 1998

[54] SERUM OR PLASMA SEPARATING COMPOSITIONS

[75] Inventors: Ryusuke Okamoto; Hideo Anraku, both of Yamaguchi, Japan

[73] Assignee: Sekisui Kagaku Kogyo Kabushiki Kaisha, Osaka, Japan

[21] Appl. No.: 809,421

[22] PCT Filed: Aug. 26, 1996

[86] PCT No.: PCT/JP96/02390

§ 371 Date: Apr. 28, 1997

§ 102(e) Date: Apr. 28, 1997

[87] PCT Pub. No.: WO97/08548

PCT Pub. Date: Mar. 6, 1997

[30] Foreign Application Priority Data

Aug. 28, 1995 [JP] Japan ................. 7-218661
Dec. 13, 1995 [JP] Japan ................. 7-324342
Apr. 26, 1996 [JP] Japan ................. 8-108083

[51] Int. Cl.$^6$ .................................. G01N 33/48
[52] U.S. Cl. ............................. 252/60; 435/2
[58] Field of Search ........................ 252/60; 435/2

[56] References Cited

U.S. PATENT DOCUMENTS

| | | | |
|---|---|---|---|
| 3,902,964 | 9/1975 | Greenspan | 435/269 |
| 4,049,692 | 9/1977 | Zine, Jr. | 210/84 |
| 4,081,432 | 3/1978 | Delente et al. | 530/384 |
| 4,101,422 | 7/1978 | Lamont et al. | 210/84 |
| 4,477,575 | 10/1984 | Vogel et al. | 436/170 |
| 5,266,219 | 11/1993 | Pall et al. | 210/767 |
| 5,298,016 | 3/1994 | Gordon | 604/4 |
| 5,364,533 | 11/1994 | Ogura et al. | 210/645 |
| 5,510,237 | 4/1996 | Isogawa et al. | 435/2 |
| 5,601,727 | 2/1997 | Bormann et al. | 210/767 |

FOREIGN PATENT DOCUMENTS

| | | |
|---|---|---|
| 53-042283A | 4/1978 | Japan |
| 56-166956A | 12/1981 | Japan |
| 57-009718A | 1/1982 | Japan |
| 01295163A | 11/1989 | Japan |
| 02095257A | 4/1990 | Japan |
| 02168159A | 6/1990 | Japan |
| 04203965A | 7/1992 | Japan |

OTHER PUBLICATIONS

Chemical Abstract No. 120:28287 which is an abstract of European Patent Specification No. 566,794 (Oct. 1993).

JAPIO Patent Abstract No. JP406003356A which is an abstract of Japanese Patent Specification No. 06–03356 (Jan. 1994).

JAPIO Patent Abstract No. JP401295163A which is an abstract of Japanese Patent Specification No. 01–295163 (Nov. 1989).

WPIDS Abstract No. 120:28287 which is an abstract of Japanese Patent Specification No. 042–03965 (Jul. 1992).

*Primary Examiner*—Anthony Green
*Attorney, Agent, or Firm*—Nikaido Marmelstein Murray & Oram, LLP.

[57] ABSTRACT

The present invention relates to a serum or plasma separating composition comprising an oligomer of cyclopentadiene, an organic gelling agent and a dispersant for the organic gelling agent. The organic gelling agent is a condensation product of sorbitol and an aromatic aldehyde. The dispersant for the organic gelling agent is a polyoxyethylene-polyoxypropylene block copolymer having HLB of 1.0 to 9.0. The invention provides a serum or plasma separating composition which does not give out a bad smell by sterilization with radiation, has no influence derived from hemolysis, etc. on biochemical examination values of serum or plasma, does not cause phase separation of components, and is equal to the prior art in serum or plasma separating property, preservation stability, etc. Furthermore, the invention provides a serum or plasma separating composition which hardly brings about flow during preservation by standing in a horizontal lying position and hardly exhibits impaired invertibility with the lapse of time.

16 Claims, No Drawings

SERUM OR PLASMA SEPARATING COMPOSITIONS

TECHNICAL FIELD

The present invention relates to serum or plasma separating compositions for use in centrifuging blood utilizing a difference in specific gravity between blood components.

BACKGROUND ART

Blood testing containers for collecting blood therein are already known which have contained in the bottom thereof a serum or plasma separating thixotropic composition such as a mixture of silicone and silica (Unexamined Japanese Patent Publication No. 83654/1976). When blood is collected in the container, allowed to stand for a suitable period of time and thereafter centrifuged, the serum or plasma separating composition, which is in the form of a gel, is fluidized by the centrifugal force. In specific gravity, the gel of the serum or plasma separating composition is intermediate between the serum or plasma and the clot or cellular (corpuscle) component of the blood, so that the composition gradually rises from the bottom of the container through the collected blood and becomes positioned between a layer of serum or plasma and a layer of blood clot or cells, separating the serum or plasma from the clot or cellular component. The serum or plasma thus separated from the clot or cellular component can be readily withdrawn from the container and subjected to various tests, or can be preserved without being transferred to another container.

The compounds already known for use as the main component of such serum or plasma separating thixotropic compositions include, in addition to the above-mentioned silicone, α-olefin-maleic acid diester copolymer (Unexamined Japanese Patent Publications No. 166956/1981 and No. 168159/1990), polyester polymer (Unexamined Japanese Patent Publication No. 233368/1986), acrylic polymer (Unexamined Japanese Patent Publication No. 42283/1978), chlorinated polybutene (Unexamined Japanese Patent Publication No. 9718/1982), cyclopentadiene resin (Unexamined Japanese Patent Publication No. 295163/1989) and modified cyclopentadiene resin prepared by introducing a hydroxyl, ester, ether, epoxy or like group into cyclopentadiene resin (Unexamined Japanese Patent Publication No. 95257/1990). The materials to be admixed with such a main component as required include, for example, inorganic fillers such as silica, which serves as specific gravity adjusting agents and also as gelling agents for giving thixotropy, substances having polar groups at opposite ends of the molecule, such as propylene glycol and ethylenediamine (such fillers and substances being disclosed in Unexamined Japanese Patent Publication No. 295163/1989), and organic gelling agents such as condensation products of sorbitol and an aromatic aldehyde (Unexamined Japanese Patent Publication No. 168159/1990).

However, silicone is poor in compatibility with the inorganic filler, undergoes a curing reaction when sterilized by radiation (e.g., gamma ray and electron ray) irradiation and is therefore almost out of use presently. α-Olefin-maleic acid diester copolymer, polyester polymer, acrylic polymer, modified cyclopentadiene resin and the like which have a polar group are relatively less likely to affect the determination of substances in the blood under clinical examination, but frequently exert an influence on the measurement of concentration of drugs in the blood (for example, the measurement of concentration of antiepileptics, such as phenobarbital, carbamazepine and phenytoin, in the blood).

On the other hand, the use of chlorinated polybutene entails the problem that when it is to be disposed of by incineration after use, the composition releases chlorine gas to cause damage to the incinerator and exert an adverse influence on the environment.

As a serum or plasma separating composition free of these drawbacks, Unexamined Japanese Patent Publication No. 203965/1992 proposes a composition comprising an oligomer of cyclopentadiene and a condensation product of sorbitol and an aromatic aldehyde as an organic gelling agent. The serum or plasma separating composition solved the above-mentioned problems of the prior art. However, dimethyl sulfoxide (DMSO) or N, N-dimethylacetamide (DMA) is used as a dispersant for the organic gelling agent. A composition containing DMSO entails the problem that sterilization by radiation (e.g., gamma ray and electron ray) irradiation decomposes DMSO in the composition to give dimethyl sulfide, which gives out a bad smell. A composition containing DMA causes the problem that DMA sometimes causes hemolysis by contacting blood, and thereby sometimes giving incorrect measured values in determining specific substances in the blood under biochemical examination.

The serum or plasma separating composition also brings about the problem that an oily component is sometimes separated from the composition during preservation. This phenomenon is referred to as phase separation hereinafter. The oily component is a low molecular weight component contained in the oligomer of cyclopentadiene in the composition. The phase separation is responsible for low compatibility of the component with the organic gelling agent and/or silica added as a specific gravity adjusting agent. If the phase separation occurs, when a blood collecting tube containing the composition is allowed to stand in a horizontal lying position or upset, the oily component adheres to a tube wall or a stopper. When blood is collected using the blood collecting tube and serum or plasma is separated from clot or cellular by centrifugation, etc., the oily component is suspended in a layer of serum or plasma. As a result, when components contained in the serum or plasma are examined, a needle for collection of serum or plasma in a detector is stopped up with the components, or the components exert influences on measured values. Furthermore, the phase separation also causes the problem that homogeneity of the composition is deteriorated and that partition wall stability is lowered.

When the serum or plasma separating composition comprising the oligomer of cyclopentadiene, the organic gelling agent and the dispersant for the organic gelling agent is contained in the bottom of the blood collecting tube and the tube is allowed to stand in a horizontal lying position and preserved (hereinafter referred to as preservation by standing in a horizontal lying position), the composition sometimes comes to flow. This phenomenon is referred to as "flow" hereinafter. When the flow takes place, the composition spreads on a side wall of the blood collecting tube. After collecting blood in the blood collecting tube, when the blood is centrifuged, the composition floats from the bottom of the tube. A partition wall which is formed between the layer of serum or plasma and the layer of blood clot or cells does not have sufficient thickness and the wall is broken by an expansion of the clot, etc. The generation of the flow is responsible for lack of thixotropy of the composition. The lack is compensated by increasing an amount of the organic gelling agent. However, the increased amount of the organic gelling agent increases thixotropy with the lapse of time and impairs invertibility in centrifuging. In the worst case, the composition fails to exhibit invertibility.

The present invention solves the above-mentioned problems. An object of the present invention is to provide a serum or plasma separating composition which does not give out a bad smell by sterilization with radiation, has no influence derived from hemolysis, etc. on biochemical examination values of the serum or plasma, does not cause phase separation of components, and is equal to the prior art in serum or plasma separating property, preservation stability, etc.

Furthermore, another object of the present invention is to provide a serum or plasma separating composition which hardly brings about the flow during preservation by standing in a horizontal lying position and hardly exhibits impaired invertibility with the lapse of time.

DISCLOSURE OF THE INVENTION

The present invention was made in order to accomplish the above-mentioned objects and provides the following compositions.

A serum or plasma separating composition comprising an oligomer of cyclopentadiene, an organic gelling agent and a dispersant for the organic gelling agent, the organic gelling agent being a condensation product of sorbitol and an aromatic aldehyde, the dispersant for the organic gelling agent being a polyoxyethylene-polyoxypropylene block copolymer having HLB of 1.0 to 9.0 (hereinafter referred to as "the first composition").

A serum or plasma separating composition comprising an oligomer of cyclopentadiene, an organic gelling agent and a dispersant for the organic gelling agent, the organic gelling agent being a condensation product of sorbitol and an aromatic aldehyde, the dispersant for the organic gelling agent comprising a polyoxyethylene-polyoxypropylene block copolymer having HLB of 1.0 to 9.0, and a tertiary amine compound having two methyl groups and an alkyl group having not less than 10 carbon atoms, the composition containing 0.03 to 0.5 part by weight of the tertiary amine compound per 100 parts by weight of the oligomer of cyclopentadiene (hereinafter referred to as "the second composition").

A serum or plasma separating composition comprising an oligomer of cyclopentadiene, a viscosity reducing agent, an organic gelling agent and a dispersant for the organic gelling agent, the oligomer of cyclopentadiene having a softening point of 70° to 140° C. and a melting viscosity of 30 to 500 centipoises (cP) at 180° C., the viscosity reducing agent being a phthalate ester, the organic gelling agent being a condensation product of sorbitol and an aromatic aldehyde, the dispersant for the organic gelling agent being selected from the group consisting of a polyoxyethylene-polyoxypropylene block copolymer having HLB of 1.0 to 9.0, 1-methyl-2-pyrrolidone and a mixture thereof (hereinafter referred to as "the third composition").

A serum or plasma separating composition comprising an oligomer of cyclopentadiene, a viscosity reducing agent, an organic gelling agent, a dispersant for the organic gelling agent and a specific gravity adjusting agent, the oligomer of cyclopentadiene having a softening point of 70° to 140° C. and a melting viscosity of 30 to 500 cP at 180° C., the viscosity reducing agent being a phthalate ester, the organic gelling agent being a condensation product of sorbitol and an aromatic aldehyde, the dispersant for the organic gelling agent being selected from the group consisting of a polyoxyethylene-polyoxypropylene block copolymer having HLB of 1.0 to 9.0, 1-methyl-2-pyrrolidone and a mixture thereof, the specific gravity adjusting agent being chlorinated paraffin, the composition containing 30 to 130 parts by weight of the viscosity reducing agent and 1 to 100 parts by weight of the specific gravity adjusting agent per 100 parts by weight of the oligomer of cyclopentadiene (hereinafter referred to as "the fourth composition").

A serum or plasma separating composition comprising an oligomer of cyclopentadiene, a compatibilizing agent, a viscosity reducing agent, an organic gelling agent and a dispersant for the organic gelling agent, the oligomer of cyclopentadiene having a softening point of 70° to 140° C. and a melting viscosity of 30 to 500 cP at 180° C., the compatibilizing agent being a styrene thermoplastic resin having a low molecular weight, the viscosity reducing agent being a phthalate ester, the organic gelling agent being a condensation product of sorbitol and an aromatic aldehyde, the dispersant for the organic gelling agent being selected from the group consisting of a polyoxyethylene-polyoxypropylene block copolymer having HLB of 1.0 to 9.0, 1-methyl-2-pyrrolidone and a mixture thereof, the composition containing 0.1 to 15 parts by weight of the compatibilizing agent per 100 parts by weight of the oligomer of cyclopentadiene (hereinafter referred to as "the fifth composition").

A serum or plasma separating composition comprising an oligomer of cyclopentadiene, a viscosity reducing agent, an organic gelling agent and a dispersant for the organic gelling agent, the oligomer of cyclopentadiene having a softening point of 70° to 140° C. and a melting viscosity of 30 to 500 cP at 180° C., the viscosity reducing agent being a phthalate ester, the organic gelling agent being a condensation product of sorbitol and an aromatic aldehyde, the dispersant for the organic gelling agent being selected from the group consisting of N,N-dimethylacetamide, N,N-dimethylformamide and a mixture thereof, the composition containing 0.01 to 0.4 part by weight of the dispersant for the organic gelling agent per 100 parts by weight of the oligomer of cyclopentadiene (hereinafter referred to as "the sixth composition").

A serum or plasma separating composition comprising a base resin and an organic gelling agent, the base resin being a polyoxyethylene-polyoxypropylene block copolymer having HLB of 1.0 to 9.0, the organic gelling agent being a condensation product of sorbitol and an aromatic aldehyde (hereinafter referred to as "the seventh composition").

The first to seventh compositions are described in detail respectively.

First Composition

First, the first composition is described, which comprises the oligomer of cyclopentadiene, the organic gelling agent and the dispersant for the organic gelling agent.

Oligomer of Cyclopentadiene

The oligomer of cyclopentadiene used in the first composition includes an oligomer prepared by polymerizing cyclopentadiene and an oligomer prepared by polymerizing dicyclopentadiene formed by dimerizing cyclopentadiene. The oligomer can be produced by polymerizing cyclopentadiene or dicyclopentadiene by, for example, Diels-Alder reaction. The oligomer is also called dicyclopentadiene resin (DCPD resin). When the oligomer is used as a component of the first composition, it is desired to saturate the remaining double bonds by hydrogenating the oligomer. The oligomer sometimes contains a trace amount of a polar residue originating from a polimerization initiator. However, since the oligomer has few polar groups in the molecule, the oligomer does not adsorb biocomponents or drugs in blood.

Unlike usual olefinic or α-olefinic polymers, the oligomer having a specific gravity of at least 1.0 can be obtained relatively easily, because the oligomer has closely packed polymer molecules. The oligomer exhibits little evaporation loss at 100° C. Accordingly, the use of the oligomer of cyclopentadiene in the serum or plasma separating composition does not cause problems such as delay of blood coagulation by volatile components, adhesion of clot on a blood collecting tube wall and giving out bad smells.

The specific gravity of the oligomer at 25° C. is preferably 1.00 to 1.10, more preferably 1.02 to 1.08, which is intermediate between specific gravity of serum or plasma and that of blood clot or cells. If the specific gravity is out of the above-mentioned range, it is difficult to adjust the specific gravity of the composition in a suitable range. The oligomer having specific gravity in the range can be easily obtained by selecting a polymerization condition, etc.

Organic gelling agent

The organic gelling agent used in the first composition is a condensation product of sorbitol and an aromatic aldehyde. Examples of the organic gelling agent are dibenzylidene sorbitol, tribenzylidene sorbitol, methyl-substituted dibenzylidene sorbitol and the like. Dibenzylidene sorbitol is especially preferable among them in terms of imparting thixotropy to the composition in blending with the oligomer of cyclopentadiene.

The gelling agent has no hygroscopicity or solubility in water, therefore will not permit the composition to absorb water and exhibit white turbidity even when the composition is held in contact with a blood sample for a long period of time and does not cause concentration of the blood sample by water absorption by the gelling agent. Additionally, since the gelling agent has both a hydrophobic group (benzyl group) and a hydrophilic group (hydroxyl group), the agent is compatible with both hydrophobic compounds and hydrophilic compounds. The gelling agent is not susceptible to phase separation even if the agent is blended with these compounds.

For the organic gelling agent to exhibit satisfactory thixotropy of the composition, it is desired that the agent is dispersed in a hydrophobic medium which is free from polar groups or reduced in polar group content. The oligomer of cyclopentadiene is suitably used as the hydrophobic medium in this respect.

If used in too small an amount, the organic gelling agent fails to give sufficient thixotropy of the composition, with the result that the composition is apt to flow during preservation and that a partition wall is easily broken in using the composition. Conversely, an excess of the agent affords excessive thixotropy of the composition, such that the partition wall becomes difficult to form even if the composition is centrifuged. Accordingly, the gelling agent is used preferably in an amount of 0.02 to 3 parts by weight, more preferably 0.02 to 1 part by weight, per 100 parts by weight of the oligomer of cyclopentadiene.

Dispersant for Organic Gelling Agent

The dispersant for the organic gelling agent used in the first composition is a polyoxyethylene-polyoxypropylene block copolymer having prescribed HLB.

If the HLB of the block copolymer is too small, the organic gelling agent cannot disperse in the block copolymer sufficiently, thixotropy of the composition is insufficient, and partition wall stability is lowered. Conversely, if the HLB is too large, hydrophobicity is insufficient, the copolymer is dissolved in blood to cause hemolysis in using the composition, and serum or plasma is contaminated by components in erythrocyte, and thereby giving incorrect biochemical examination results. Accordingly, the HLB is 1.0 to 9.0, preferably 4.0 to 6.0.

The HLB has been used as an indication showing a degree of hydrophilicity and hydrophobicity of a general non-ionic surfaceactive agent having structure of hydrophilic site-hydrophobic site, and defined by the Griffin's equation. However, the equation cannot be applied to substances having structure of hydrophilic site-hydrophobic site-hydrophilic site such as the block copolymer used in the composition. The HLB of the present invention is defined by the following empirical equation.

HLB=0.098×(Clouding point of the block copolymer measured by the following method)+4.02

The clouding point is measured by the following method. In 5 ml of a 98% aqueous ethanol solution is dissolved 0.5 g of the block copolymer. The obtained solution is kept at 25° C. and titrated with a 2% aqueous phenol solution while stirring at 25° C. A final point is shown by a turbidity of the solution. The clouding point is defined as the volume expressed in ml of the 2% aqueous phenol solution required for the titration.

Various grades of the block copolymers are commercially available from many makers. Any block copolymers having the HLB of 1.0 to 9.0 can be used without limitation.

If used in too small an amount, the dispersant for the organic gelling agent gives lowered dispersion of the organic gelling agent and insufficient thixotropy of the composition. Conversely, an excess of the dispersant affords a lowered viscosity of the composition, lowered compatibility with the oligomer of cyclopentadiene, and lowered thixotropy of the composition. Accordingly, the dispersant is used preferably in an amount of 0.1 to 15 parts by weight, more preferably 0.1 to 5 parts by weight, per 100 parts by weight of the oligomer of cyclopentadiene.

Specific Gravity Adjusting Agent

When desired, a specific gravity adjusting agent may be added to the first composition to thereby adjust the specific gravity of the serum or plasma separating composition to a desired value. Examples of the specific gravity adjusting agent are finely divided inorganic materials such as silica, bentonite and titanium oxide, and finely divided polymers such as polystyrene and polyurethane. The specific gravity adjusting agent is preferably up to 500 μm in mean particle size so as to be mixed and dispersed in the composition with ease.

If an amount of the specific gravity adjusting agent is too large, the oligomer of cyclopentadiene and the specific gravity adjusting agent are liable to separate owing to a great difference therebetween in specific gravity. Accordingly, the agent is used preferably in an amount of up to 50 parts by weight, more preferably up to 10 parts by weight, per 100 parts by weight of the oligomer.

Viscosity Reducing Agent

When desired, furthermore, a viscosity reducing agent may be added to the first composition to thereby adjust the viscosity. Insofar as the viscosity reducing agent does not influence blood components or blood coagulation, any agents can be used without limitation. For example, a phthalate ester or a benzoate ester is suitable.

If an amount of the viscosity reducing agent is too large, the oligomer and the oligomer of cyclopentadiene are liable to separate owing to a great difference therebetween in specific gravity. Accordingly, the agent is used preferably in an amount of up to 50 parts by weight, more preferably up to 10 parts by weight, per 100 parts by weight of the oligomer.

Suitable Specific Gravity of Composition

The specific gravity of the first composition is preferably intermediate between specific gravity of serum or plasma and that of blood clot or cells. In practice, the specific gravity is preferably 1.03 to 1.08, more preferably 1.04 to 1.06 at 25° C.

Suitable Viscosity of Composition

A viscosity of the first composition is preferably 50,000 to 1,000,000 cP, more preferably 60,000 to 500,000 cP at 25° C. so that the composition is positioned between a layer of serum or plasma and a layer of blood clot or cells by usual centrifugation and that the composition is easily contained in a blood testing container such as a blood collecting tube.

Usage

The first composition is used generally as contained in a container having a bottom and serving as a blood collecting tube of the vaccum type or non-vaccum type. When blood is collected in the container by a specified method and then centrifuged for separation, the blood separates into the serum or plasma, and the clot or solid components in blood such as blood cells owing to a difference in specific gravity therebetween, such that the composition is positioned between the serum or plasma part in an upper position and the blood clot part or the solid components in blood in a lower position, thus serving as a partition wall therebetween to perform the function of separating composition.

Second Composition

Next, the second composition is described, which comprises the oligomer of cyclopentadiene, the organic gelling agent and the dispersant for the organic gelling agent.

Dispersant for Organic Gelling Agent

The dispersant for the organic gelling agent used in the second composition comprises a polyoxyethylene-polyoxypropylene block copolymer having HLB of 1.0 to 9.0 and a tertiary amine having two methyl groups and an alkyl group having not less than 10 carbon atoms.

The block copolymer and an amount thereof may be the same as those stated in the description of the first composition.

The tertiary amine has the two methyl groups and the alkyl group having not less than 10 carbon atoms. A tertiary amine having only one methyl group causes the flow of the obtained composition and fails to exhibit sufficient addition effects thereof. A tertiary amine having not more than 9 carbon atoms lowers compatibility of the tertiary amine with the oligomer of cyclopentadiene and fails to exhibit sufficient addition effects thereof. Examples of the tertiary amine are dodecyldimethylamine, tetradecyldimethylamine, hexadecyldimethylamine and the like.

If used in too small an amount, the amine is liable to cause the flow of the composition. Conversely, an excess of the amine affords excessive thixotropy and impaired invertibility of the composition. Accordingly, the amine is used preferably in an amount of 0.03 to 0.5 part by weight, more preferably 0.05 to 0.3 part by weight, per 100 parts by weight of the oligomer of cyclopentadiene.

The oligomer of cyclopentadiene and the organic gelling agent being other essential components of the second composition, the specific gravity adjusting agent and the viscosity reducing agent being optionally added components of the second composition, amounts thereof, a suitable specific gravity, a suitable viscosity and usage may be the same as those stated in the description of the first composition.

Third Composition

The third composition is described, which comprises the oligomer of cyclopentadiene, the viscosity reducing agent, the organic gelling agent and the dispersant for the organic gelling agent.

Oligomer of Cyclopentadiene

The oligomer of cyclopentadiene used in the third composition is the oligomer of the first composition and has a softening point of 70° to 140° C. and a melting viscosity of 30 to 500 cP at 180° C.

If the softening point of the oligomer is too low, the composition is susceptible to phase separation. Conversely, if the softening point is too high, the composition becomes difficult to melt, with the result that the composition becomes difficult to produce. Accordingly, the softening point is 70° to 140° C., preferably 80° to 110° C. The softening point is me as u red by JIS K6863-1994 "method of testing softening point of hot melt adhesives".

If the melting viscosity of the oligomer at 180° C. is too low, the composition has an insufficient viscosity. Conversely, if the melting viscosity is too high, the composition has a high viscosity at low temperatures, such that the composition becomes difficult to use. Accordingly, the melting viscosity is 30 to 500 cP, preferably 100 to 500 cP. The melting viscosity is measured by the "A method" in JIS K6862-1984 "method of testing melting viscosity of hot melt adhesives" with "B type viscometer" manufactured by Brookfield Co., Ltd. using "A-1 type rotor".

In particular, the oligomer of cyclopentadiene used in the third composition preferably has the following physical properties.

Specific Gravity

A specific gravity at 25° C. (by a sink and float test using a cupper sulfate solution) is 1.02 to 1.10, preferably 1.03 to 1.09. When the specific gravity is out of the above-mentioned range, it is sometimes difficult to adjust a specific gravity of the composition suitably.

Molecular Weight

A molecular weight distribution by the GPC method is 200 to 500, preferably 300 to 450 expressed in number-average molecular weight and 600 to 900, preferably 700 to 850 expressed in weight-average molecular weight. If each molecular weight is lower than the lower limit of the above-mentioned range, a low molecular weight fraction can be substantially contained in the composition, and thereby permitting phase separation. Conversely, if each molecular weight exceeds the upper limit of the range, the viscosity of the resin increases so that it can be difficult to obtain an effect of the viscosity reducing agent.

Glass Transition Point

A glass transition point by the DSC method is 50° to 90° C., preferably 60° to 80° C. If the glass transition point is lower than the lower limit of the above-mentioned range, the low molecular weight fraction can be substantially contained in the composition, and thereby permitting phase separation. Conversely, if the glass transition point exceeds the upper limit of the range, the viscosity of the resin increases so that it can be difficult to obtain the effect of the viscosity reducing agent.

Weight Loss-Starting Temperature

A weight loss-starting temperature by the TG method is 100° to 400° C., preferably 120° to 350° C. If the weight loss-starting temperature is lower than the lower limit of the above-mentioned range, the low molecular weight fraction can be substantially contained in the composition, and thereby permitting phase separation. Conversely, if the weight loss-starting temperature exceeds the upper limit of the range, the viscosity of the resin increases so that it can be difficult to obtain the effect of the viscosity reducing agent.

Viscosity Reducing Agent

The viscosity reducing agent used in the third composition is a phthalate ester from the viewpoint of excellent compatibility with the oligomer of cyclopentadiene. The phthalate ester is preferably a phthalate diester. In the diester, between two alcohol residues forming each ester group, at least one alcohol residue preferably has not less than 6 carbon atoms. A diester having alcohol residues having not more than 5 carbon atoms respectively tends to lower compatibility with the oligomer of cyclopentadiene. The number of carbon atoms of each alcohol residue is preferably not more than 11 because it is difficult to adjust the specific gravity of the composition in a suitable range if the number is too large.

Examples of the viscosity reducing agent used in the third composition are butyl pentyl phthalate, dipentyl phthalate, butyl hexyl phthalate, butyl heptyl phthalate, dihexyl phthalate, pentyl heptyl phthalate, butyl nonyl phthalate, pentyl octyl phthalate, hexyl heptyl phthalate, diheptyl phthalate, heptyl octyl phthalate, dioctyl phthalate, di(2-ethylhexyl) phthalate, octyl nonyl phthalate, diisononyl phthalate, octyl decyl phthalate, diisodecyl phthalate, decyl undecyl phthalate, diundecyl phthalate and butyl benzyl phthalate.

Particularly preferred viscosity reducing agent is a phthalate diester wherein the number of carbon atoms of each alcohol residue is 9 to 11. The most preferred viscosity reducing agents are di(2-ethylhexyl) phthalate and dioctyl phthalate in terms of adjustment of the specific gravity of the composition.

If used in too small an amount, the viscosity reducing agent used in the third composition gives a high viscosity of the composition, such that the composition becomes difficult to use. Conversely, an excess of the agent gives a too low viscosity of the composition to use the composition, and it becomes difficult to adjust the specific gravity of the composition. Accordingly, the agent is used preferably in an amount of 30 to 130 parts by weight, more preferably 50 to 100 parts by weight, per 100 parts by weight of the oligomer of cyclopentadiene.

Dispersant for Organic Gelling Agent

The dispersant for the organic gelling agent used in the third composition is selected from the group consisting of a polyoxyethylene-polyoxypropylene block copolymer having HLB of 1.0 to 9.0, 1-methyl-2-pyrrolidone and a mixture thereof.

The polyoxyethylene-polyoxypropylene block copolymer and an amount thereof may be the same as those stated in the description of the first composition.

1-Methyl-2-pyrrolidone is suitably used because it dissolve the organic gelling agent well, it does not cause hemolysis by a reaction with blood, and it does not give out a bad smell by decomposition by irradiation with radiation.

If used in too small an amount, 1-methyl-2-pyrrolidone gives lowered dispersion of the organic gelling agent and insufficient thixotropy of the composition. Conversely, an excess of 1-methyl-2-pyrrolidone causes hemolysis. Accordingly, 1-methyl-2-pyrrolidone is used preferably in an amount of 0.05 to 5 parts by weight, more preferably 0.05 to 3 parts by weight, per 100 parts by weight of the oligomer of cyclopentadiene.

The organic gelling agent being another essential component of the third composition, the specific gravity adjusting agent and the viscosity reducing agent being optionally added components of the third composition, amounts thereof, a suitable specific gravity, a suitable viscosity and usage may be the same as those stated in the description of the first composition.

Fourth Composition

The fourth composition is described, which comprises the oligomer of cyclopentadiene, the viscosity reducing agent, the organic gelling agent, the dispersant for the organic gelling agent and the specific gravity adjusting agent.

Specific Gravity Adjusting Agent

The specific gravity adjusting agent used in the fourth composition is chlorinated paraffin. Since the paraffin is chemically inactive, insoluble in water, odorless and harmless, it is suitable for a component for the serum or plasma separating composition.

The chlorinated paraffin has chlorination degrees of 40%, 45%, 50%, 65% and 70%, and any of them can be used. Since the chlorinated paraffin has a specific gravity of 1.15 to 1.70 at 25° C., it is suitable for the specific gravity adjusting agent.

If an amount of the specific gravity adjusting agent is too large, the oligomer of cyclopentadiene and the specific gravity adjusting agent are liable to separate owing to a great difference therebetween in specific gravity. Conversely, if used in too small an amount, the agent fails to exhibit a sufficient specific gravity adjusting effect. Accordingly, the agent is used preferably in an amount of 1 to 100 parts by weight, more preferably 5 to 60 parts by weight, per 100 parts by weight of the oligomer.

The oligomer of cyclopentadiene, the viscosity reducing agent, the organic gelling agent and the dispersant for the organic gelling agent being other essential components of the fourth composition, amounts thereof, a suitable specific gravity, a suitable viscosity and usage may be the same as those stated in the description of the third composition.

Fifth Composition

The fifth composition is described, which comprises the oligomer of cyclopentadiene, the compatibilizing agent, the viscosity reducing agent, the organic gelling agent and the dispersant for the organic gelling agent.

Compatibilizing Agent

The compatibilizing agent used in the fifth composition is a low molecular weight styrene thermoplastic resin such as low molecular weight polystyrene. The low molecular weight styrene thermoplastic resin preferably has a softening point by JIS K6863-1994 of 130° to 180° C., a specific gravity by the sink-float method of 1.03 to 1.07 at 25° C., number-average molecular weight by the GCP method of 34,000 to 46,000, and weight-average molecular weight by the GCP method of 69,000 to 91,000. If used in too small an amount, the compatibilizing agent exhibits an insufficient compatibilizing effect to cause phase separation. Conversely, an excess of the agent affords a high viscosity of the composition to prevent inversion. Accordingly, the agent is used in an amount of 0.1 to 15 parts by weight, preferably 0.5 to 10 parts by weight, per 100 parts by weight of the oligomer of cyclopentadiene.

The oligomer of cyclopentadiene, the viscosity reducing agent, the organic gelling agent and the dispersant for the organic gelling agent being other essential components of the fifth composition, the specific gravity adjusting agent being an optionally added component of the fifth composition, amounts thereof, a suitable specific gravity, a suitable viscosity and usage may be the same as those stated in the description of the fourth composition.

Sixth Composition

The sixth composition is described, which comprises the oligomer of cyclopentadiene, the viscosity reducing agent, the organic gelling agent and the dispersant for the organic gelling agent.

Dispersant for Organic Gelling Agent

The dispersant for the organic gelling agent used in the sixth composition is selected from the group consisting of N, N-dimethylacetamide (DMA), N,N-dimethylformamide (DMF) and a mixture thereof.

If used in too small an amount, the dispersant for the organic gelling agent of the sixth composition fails to exhibit a sufficient dispersion effect and thixotropy of the organic gelling agent, and a partition wall is not good in stability. Conversely, if the amount of the dispersant is too large, the blood contacting the composition is subjected to hemolysis in collecting the blood, and thereby exerting an adverse effect on examination values. Accordingly, the dispersant is used in an amount of 0.01 to 0.4 part by weight, preferably 0.05 to 0.4 part by weight, per 100 parts by weight of the oligomer of cyclopentadiene.

The oligomer of cyclopentadiene, the viscosity reducing agent and the organic gelling agent being other essential components of the sixth composition, the specific gravity adjusting agent being an optionally added component of the sixth composition, amounts thereof, a suitable specific gravity, a suitable viscosity and usage may be the same as those stated in the description of the fourth composition.

Seventh Composition

Finally, the seventh composition is described, which comprises the base resin and the organic gelling agent.

The polyoxyethylene-polyoxypropyrene block copolymer which is used as the base resin in the seventh composition and has prescribed HLB may be the same as that used as the dispersant for the organic gelling agent in the first composition.

The organic gelling agent may also be the same as that stated in the description of the first composition.

If used in too small an amount, the organic gelling agent fails to give sufficient thixotropy of the composition, with the result that the composition is apt to flow during preservation and that a partition wall is easily broken in using the composition. Conversely, an excess of the agent affords excessive thixotropy of the composition, such that the partition wall is difficult to form even if the composition is centrifuged. Accordingly, the gelling agent is used preferably in an amount of 5 to 100 parts by weight, more preferably 20 to 70 parts by weight, per 100 parts by weight of the polyoxyethylene-polyoxypropyrene block copolymer.

When desired, a specific gravity adjusting agent and/or a viscosity reducing agent may also be added to the seventh composition.

If amounts of the specific gravity adjusting agent and the viscosity reducing agent are too large, the dispersant and the specific gravity adjusting agent are liable to separate owing to a great difference therebetween in specific gravity. Accordingly, the agents are used preferably in amounts of up to 40 parts by weight, more preferably up to 20 parts by weight, per 100 parts by weight of the block copolymer respectively.

A suitable specific gravity, a suitable viscosity and usage of the seventh composition may be the same as those stated in the description of the first composition.

Since the compositions of the present invention are constituted as above, the compositions act as follows.

Action of the First to Sixth Compositions

A conventional serum or plasma separating composition comprising an oligomer of cyclopentadiene and a condensation product of sorbitol and an aromatic aldehyde as an organic gelling agent was prepared by dissolving the organic gelling agent in an organic solvent such as DMSO or DMA, and then blending the obtained solution with a homogeneous mixture of the oligomer of cyclopentadiene and a finely divided inorganic material such as finely divided silica by the gaseous phase method.

However, the organic solvent remains in the composition, decomposes by irradiation with radiation to give out a bad smell, or act on blood to cause hemolysis, and thereby sometimes exerting an ill influence on biochemical examination values.

Since the specific polyoxyethylene-polyoxypropyrene block copolymer is used as the dispersant for the organic gelling agent in the first to sixth compositions of the present invention, the organic solvent such as DMSO or DMA is not required. Accordingly, the compositions do not give malodorous substances by irradiation with radiation. Unlike the organic solvent, the dispersant itself can participate in hydrogen bonding together with the organic gelling agent and finely divided silica, and exhibit better thixotropy than the conventional composition. In addition, since the dispersant is a hydrophobic high-molecular weight compound, the dispersant also has an advantage of not causing hemolysis, etc. by partially dissolving in blood, serum or plasma.

Action of the Second Composition

Though the composition of the present invention is excellent in storage stability, the organic gelling agent gradually disperses in the oligomer of cyclopentadiene during long-term preservation, and thixotropy is liable to rise with the lapse of time.

In the second composition, the organic gelling agent is homogeneously dispersed in the oligomer of cyclopentadiene for a short time by the combined action of the polyoxyethylene-polyoxypropyrene block copolymer and the tertiary amine as the dispersant, and thereby preventing both poor invertibility by the rise in thixotropy with the lapse of time and the flow.

Action of the Third to Sixth Compositions

In the conventional serum or plasma separating composition comprising the oligomer of cyclopentadiene, the organic gelling agent, etc., an oily component separated by phase separation is mainly a low molecular weight component contained in the oligomer of cyclopentadiene in the composition and is contaminated by a part of the viscosity reducing agent, the organic gelling agent, etc.

In the third to sixth compositions, since an oligomer of cyclopentadiene containing a very small amount of the low molecular weight component is used, the compositions are not susceptible to phase separation of components. The oligomer of cyclopentadiene is a solid at ordinary temperature, but the oligomer is apt to flow at ordinary temperature by adding the viscosity reducing agent thereto. The third to sixth compositions obtained by adding the specific organic gelling agent, the specific dispersant, and if necessary, the specific gravity adjusting agent to the oligomer of cyclopentadiene containing the viscosity reducing agent have thixotropy and specific gravity being in suitable ranges for the serum or plasma separating compositions, and substantially do not permit phase separation.

Action of the Fifth Composition

When an oligomer of cyclopentadiene having a specific softening point and a specific melting viscosity is used, the composition substantially do not permit phase separation. However, a trace amount of the viscosity reducing agent can be separated from the composition. In particular, when longer term of effectiveness than that of the conventional blood collecting tube is guaranteed, phase separation can take place.

In the fifth composition, addition of the compatibilizing agent can increase compatibility of the oligomer with the viscosity reducing agent to prevent phase separation almost completely.

Action of the Sixth Composition

In the conventional composition, addition of an effective amount of DMA and/or DMF as the dispersant of the organic gelling agent causes hemolysis.

The sixth composition can exhibit a dispersion effect equal to that of the conventional composition in a smaller amount of DMA and/or DMF by using the oligomer of cyclopentadiene having a specific softening point and a specific melting viscosity, and the viscosity reducing agent, and adding the organic gelling agent and DMA and/or DMF as the dispersant of the organic gelling agent. As a result, hemolysis is not caused by a decrease in concentration of the dispersant.

Action of the Seventh Composition

In the prior art, network structure by hydrogen bonding of the organic gelling agent and silica exhibits thixotropy. The oligomer of cyclopentadiene being the base resin does not participate in thixotropy.

On the other hand, in the seventh composition, since network structure by simple hydrogen bonding of the organic gelling agent exhibits thixotropy, the network structure does not change with the lapse of time unlike the conventional composition. Accordingly, the seventh composition is less susceptible to phase separation.

In the prior art, silica added to the composition tends to agglomerate again after being dispersed in the oligomer of cyclopentadiene. In these stages, a low molecular weight component tends to be pushed out of the network structure of the silica and the organic gelling agent to promote phase separation.

In the seventh composition, the organic gelling agent mainly participates in imparting thixotropy. Hence, when a little silica is used as the specific gravity adjusting agent, phase separation is not promoted even if the silica agglomerates again.

Since the polyoxyethylene-polyoxypropylene block copolymer is a non-ionic surface-active agent, it disperses the organic gelling agent homogeneously, and exhibits good thixotropy. In addition, since the copolymer has HLB of 1.0 to 9.0 and is far more hydrophobic than general non-ionic surface-active agents, the copolymer is hardly compatible with blood, and thereby exerting no adverse effect on biochemical examination values of blood.

Furthermore, the polyoxyethylene-polyoxypropylene block copolymer has a less temperature-dependent viscosity than the conventional oligomer of cyclopentadiene. Accordingly, the seventh composition is far less temperature-dependent than the conventional composition and is not susceptible to poor separation of serum or plasma in centrifuging at low temperatures, which has so far become an issue.

BEST MODE FOR CARRYING OUT THE INVENTION

The present invention will be described with reference to Examples and Comparative Examples given below. The compositions obtained were tested for the evaluation of performance.

In each Example, the number (i) represents an oligomer of cyclopentadiene. The number (ii) represents a viscosity reducing agent. The number (iii) represents an organic gelling agent. The number (iv) represents a dispersant for the organic gelling agent (a base resin in Example 19 and Comparative Examples 19 and 20 corresponding to the seventh composition). The number (v) represents a specific gravity adjusting agent. The number (vi) represents a compatibilizing agent.

The specific gravity was measured by the sink and float method in a constant-temperature chamber at about 25° C. using copper sulfate solutions. The viscosity was measured at 25° C. using a Brookfield E-type viscometer at a rotational speed of 1.0 r.p.m.

Incidently, examples 1 and 2 and Comparative Examples 1 to 5 correspond to the first composition. Example 3 and Comparative Examples 6 to 8 correspond to the second composition. Examples 4 to 8 and Comparative Example 9 correspond to the third composition. Examples 9 to 13 and Comparative Examples 10 to 14 correspond to the fourth composition. Examples 14 and 15 and Comparative Examples 15 and 16 correspond to the fifth composition. Examples 16 to 18 and Comparative Examples 17 and 18 correspond to the sixth composition. Example 19 and Comparative Examples 19 and 20 correspond to the seventh composition.

The materials used as compounding ingredients of the compositions are shown below.

(i) Oligomer of Cyclopentadiene

Oligomer of dicyclopentadiene A: hydrogenated cyclopentadiene resin, "ECR-327S" manufactured by Exxon Chemical Co., Ltd., specific gravity: 1.04

Oligomer of dicyclopentadiene B: "LL101" manufactured by Nippon Zeon Co., Ltd., specific gravity: 1.04

Oligomer of cyclopentadiene C: "KR242" manufactured by Tonex Co., Ltd., softening point: 106° C., melting viscosity at 180° C.: 320 cP, specific gravity: 1.07, number-average molecular weight: about 400, weight-average molecular weight: about 800, glass transition point: about 75° C., weight loss-starting temperature: about 200° C.

Oligomer of cyclopentadiene D: "KR240" manufactured by Tonex Co., Ltd., softening point: 85° C., melting viscosity at 180° C.: 72 cP, specific gravity: 1.073, number-average molecular weight: about 350, weight-average molecular weight: about 750, glass transition point: about 65° C., weight loss-starting temperature: about 130° C.

(ii) Viscosity Reducing Agent

Viscosity reducing agent A: phthalate diester wherein each alcohol residue is an alkyl group having 9 to 11 carbon atoms, "PL-200" manufactured by Mitsubishi Gas Chemical Co., Inc.

Di(2-ethylhexyl) phthalate: "DOP" manufactured by Sekisui Chemical Co., Ltd.

(iii) Organic Gelling Agent

Dibenzylidenesorbitol: "Gelol D" manufactured by Shin-nihon Rika Co., Ltd.

(iv) Dispersant for Organic Gelling Agent

Dispersant for organic gelling agent A: polyoxyethylene-polyoxypropylene block copolymer "ADKPluronic L-121" manufactured by Asahi Denka Kogyo KK., HLB: 5.1

Dispersant for organic gelling agent B: polyoxyethylene-polyoxypropylene block copolymer "ADK Pluronic L-44" manufactured by Asahi Denka Kogyo K.K., HLB: 9.5

1-Methyl-2-pyrrolidone: manufactured by Wako Pure Chemical Industries, Ltd.

DMSO: manufactured by Wako Pure Chemical Industries, Ltd.

DMA: manufactured by Wako Pure Chemical Industries, Ltd.

DMF: manufactured by Wako Pure Chemical Industries, Ltd.

Hexadecyldimethylamine: "Nissan tertiary amine PB" manufactured by Nippon Oils & Fats Co., Ltd.

(v) Specific Gravity Adjusting Agent

Finely divided silica A: finely divided silica by the gaseous phase method, "DM-30S" manufactured by Tokuyama Co., Ltd.

Finely divided silica B: finely divided silica by the gaseous phase method, "Aerosil R-812" manufactured by Nippon Aerosil Co., Ltd.

Titanium oxide: "Tipaque A-100" manufactured by Yasuhara Sangyo Co., Ltd.

Chlorinated paraffin A: manufactured by Wako Pure Chemical Industries, Ltd., chlorination degree: 40%

Chlorinated paraffin B: manufactured by Wako Pure Chemical Industries, Ltd., chlorination degree: 70%

(vi) Compatibilizing Agent

Low molecular weight styrene thermoplastic resin: "DIC Elastyrene #200" manufactured by Dainippon Ink & Chemicals Inc.

In each performance test, the symbol "n" represents a number of repeating.

EXAMPLE 1

| | |
|---|---|
| (i) Oligomer of dicyclopentadiene A | 100 parts by weight |
| (ii) Viscosity reducing agent A | 5.40 parts by weight |
| (iii) Dibenzylidenesorbitol | 0.13 part by weight |
| (iv) Dispersant for organic gelling agent A | 0.52 part by weight |
| (v) Finely divided silica B | 2.30 parts by weight |

They were kneaded under reduced pressure for one hour to prepare a composition. The composition had a specific gravity of 1.05 and a viscosity of about 140,000 cP at 25° C.

EXAMPLE 2

A composition obtained in the same manner as in Example 1 was subjected to the tests mentioned below.

Comparative Example 1

A composition was prepared in the same manner as in Example 1 except that 0.52 part by weight of DMSO was used in place of the dispersant for the organic gelling agent A as the component (iv).

Comparative Example 2

A composition obtained in the same manner as in Comparative Example 1 was subjected to the tests mentioned below.

Comparative Example 3

A composition was prepared in the same manner as in Example 1 except that 0.52 part by weight of DMA was used in place of the dispersant for the organic gelling agent A as the component (iv).

Comparative Example 4

A composition obtained in the same manner as in Comparative Example 3 was subjected to the tests mentioned below.

Comparative Example 5

A composition was prepared in the same manner as in Example 1 except that 0.52 part by weight of a dispersant for the organic gelling agent B was used in place of the dispersant for the organic gelling agent A as the component (iv).

Evaluation of Performance

The serum or plasma separating compositions obtained in Example 1 and Comparative Examples 1, 3 and 5 were tested for evaluation of performance with respect to the following items.

About 1.2 g of the composition was placed in the bottom of a commercially available polyethylene terephthalate blood collecting tube having volume of 10 ml and an opening of the tube was closed with a stopper made of butyl rubber in vacuo. The blood testing container produced in this manner was subjected to the following tests.

1) Radiation irradiation test (n=50)

The container was irradiated with gamma rays originating from cobalt-60 having a dose of 25±7 kGray. After irradiation, the container was opened, and the composition was smelled to evaluate the smell organoleptically.

2) Invertibility test and partition wall stability test

A 4 ml quantity of fresh rabbit blood was injected into the blood testing container. After recognizing the completion of coagulation of the blood, the container was centrifuged at 15° C. and 1300 G for 10 minutes. It was observed whether the serum separating composition floated from the bottom of the testing tube and formed a partition wall between serum and clot (invertibility test). The thickness of the partition wall was also measured.

In addition, after centrifuging, the blood testing container was allowed to stand in a horizontal lying position for two weeks, the partition wall was checked for the flow (deformation) (partition wall stability test).

3) Measurement of biochemical examination values (n=3)

A 4 ml quantity of fresh rabbit blood was injected into the blood testing container. After recognizing the completion of coagulation of the blood, the container was centrifuged at 15° C. and 1300 Gfor 10 minutes, and the separated serum layer was dispensed. No oily component was observed in the obtained serum. The serum was subjected to biochemical examination with respect to the following three items. As a reference test, the dispensed serum was tested using a blood testing container produced in the same manner as mentioned above except that the separating composition was not placed into the container. (The analysis was entrusted to Fukuyama Rinsho Clinical Examination Center.)

Item a: lactate dehydrogenase

Item b: creatine phosphokinase

Item c: hydroxybutylate dehydrogenase

The serum or plasma separating compositions obtained in Example 2 and Comparative Examples 2 and 4 were tested in the same manner as in the test of the composition of Example 1 except that the blood testing container was irradiated with accelerated electron rays having a dose of 20±10 kGray in 1) radiation irradiation test.

The test results are shown in Table 1.

TABLE 1

| | Bad smell by radiation | Invertibility Thickness of partition | | Biochemical examination value (Measured value/Reference value) | | |
|---|---|---|---|---|---|---|
| | irradiation | wall | Flow | Item a | Item b | Item c |
| Example 1 | Not detected | ≧7 mm | None | 0.99 | 0.99 | 1.00 |
| Example 2 | Not detected | ≧7 mm | None | 1.00 | 0.99 | 0.97 |
| Comparative Example 1 | Detected | ≧7 mm | None | 1.02 | 0.98 | 0.97 |
| Comparative Example 2 | Detected | ≧7 mm | None | 1.00 | 0.98 | 1.02 |
| Comparative Example 3 | Not detected | ≧7 mm | None | 1.89 | 1.71 | 1.90 |
| Comparative Example 4 | Not detected | ≧7 mm | None | 1.77 | 1.59 | 1.63 |
| Comparative Example 5 | Not detected | ≧7 mm | None | 1.65 | 1.87 | 1.59 |

In Table 1, when a bad smell of dimethyl sulfide was detected, the bad smell is indicated as "Detected". Conversely, when the bad smell was not detected, it is indicated as "Not detected". If the thickness of the partition wall is not less than 5 mm, it is usually good. When the flow of the partition wall occurs, partition wall stability becomes insufficient. Accordingly, when the blood testing container is preserved as it is after centrifuging, a clot layer intrudes again into the serum layer which has already been separated. The expression "None" of the flow means that the partition wall is stable and that the flow is not liable to take place. In a biochemical examination, if the ratio of a measured value to a reference value (measured value/reference value) is 0.90 to 1.10, the ratio is generally allowed in a clinical examination.

The measured values of the components in the serum obtained using the compositions of Examples 1 and 2 are equal to those of the reference test in any items. The compositions were found to exert no adverse effect on the biochemical examination. The measured values of the components in the serum obtained using the compositions of Comparative Examples 1 to 5 are larger than those of the reference test in any items. The compositions of Comparative Examples 1 to 5 did not give correct measured values.

EXAMPLE 3

| | |
|---|---|
| (i) Oligomer of dicyclopentadiene B | 100 parts by weight |
| (ii) Viscosity reducing agent A | 6.00 parts by weight |
| (iii) Dibenzylidenesorbitol | 0.82 part by weight |
| (iv) Dispersant for organic gelling agent A | 0.82 part by weight |
| (iv) Hexadecyldimethylamine | 0.22 part by weight |
| (v) Finely divided silica A | 1.98 parts by weight |

They were kneaded under reduced pressure for one hour to prepare a composition. The composition had a specific gravity of 1.05 and a viscosity of about 250,000 cP at 25° C.

Comparative Example 6

A composition was prepared in the same manner as in Example 3 except that the component (iv) hexadecyldimethylamine was used in an amount of 0.02 part by weight and that the component (ii) viscosity reducing agent A was used in an amount of 6.18 parts by weight. The composition had a specific gravity of 1.05 and a viscosity of about 200,000 cP at 25° C.

Comparative Example 7

A composition was prepared in the same manner as in Example 3 except that the component (iv) hexadecyldimethylamine was used in an amount of 0.66 part by weight and that the component (ii) viscosity reducing agent A was used in an amount of 5.55 parts by weight. The composition had a specific gravity of 1.05 and a viscosity of about 400,000 cP at 25° C.

Comparative Example 8

| | |
|---|---|
| (i) Oligomer of dicyclopentadiene B | 100 parts by weight |
| (ii) Viscosity reducing agent A | 6.20 parts by weight |
| (iii) Dibenzylidenesorbitol | 0.82 part by weight |
| (iv) DMSO | 0.82 part by weight |
| (v) Finely divided silica A | 1.98 parts by weight |

They were kneaded under reduced pressure for one hour to prepare a composition. The composition had a specific gravity of 1.05 and a viscosity of about 200,000 cP at 25° C.

Evaluation of Performance

The serum or plasma separating compositions obtained in Example 3 and Comparative Examples 6 to 8 were tested for evaluation of performance with respect to the following items.

Blood testing containers were produced from the compositions in the same manner as in the test of the composition of Example 1 and subjected to the following tests.

1) Flow test (n=5)

The blood testing container was kept horizontally at 60° C. and allowed to stand for 7 days. A distance between a contact point of the composition before test with the inside of the tube and the tip of the flow of the composition after test was measured.

2) Invertibility test and partition wall stability test (n=5)

The composition was subjected to invertibility test and partition wall stability test in the same manner as in the test of the composition of Example 1.

The test results are shown in Table 2.

TABLE 2

| | Flow (Average ± Standard deviation) | Invertibility (Thickness of partition wall) | Partition wall stability |
|---|---|---|---|
| Example 3 | 2.5 ± 0.4 mm | ca. 6 mm | Good |
| Comparative Example 6 | 33.5 ± 2.0 mm | ca. 2 mm | Poor |
| Comparative Example 7 | 0.8 ± 0.1 mm | No partition wall was formed. | Poor |
| Comparative Example 8 | 35.5 ± 2.5 mm | ca. 2 mm | Poor |

In Table 2, if the thickness of the partition wall is not less than 5 mm, it is usually good. If the flow is not more than 10 mm, it is good. When the partition wall was not deformed even two weeks after standing, the partition wall stability is indicated as "Good". Conversely, when the partition wall was broken or not formed, and serum and clot could not be separated, the stability is indicated as "Poor".

EXAMPLE 4

| (i) Oligomer of cyclopentadiene C | 100 parts by weight |
|---|---|
| (ii) Viscosity reducing agent A | 66.6 parts by weight |
| (iii) Dibenzylidenesorbitol | 0.1 part by weight |
| (iv) Dispersant for organic gelling agent A | 0.1 part by weight |
| (iv) 1-Methyl-2-pyrrolidone | 0.3 part by weight |
| (v) Finely divided silica A | 5.9 parts by weight |

The component (i) was melted by heating at 130° C. To the resulting melt were added the components (ii)–(iv), and the mixture was kneaded for 30 minutes. After cooling to ordinary temperature, the component (v) was added thereto. The obtained mixture was kneaded in a vaccum for 30 minutes to give a composition. The obtained composition had a specific gravity of 1.05 at 25° C. and a viscosity of about 160,000 cP at 25° C.

EXAMPLE 5

A composition was prepared in the same manner as in Example 4 except that the component (iv) was used in an amount of 0.4 part by weight and that 1-methyl-2-pyrrolidone was not used. The obtained composition had a specific gravity of 1.05 at 25° C. and a viscosity of about 160,000 cP at 25° C.

EXAMPLE 6

A composition was prepared in the same manner as in Example 4 except that the component (iv) was not used and that 1-methyl-2-pyrrolidone was used in an amount of 0.4 part by weight. The obtained composition had a specific gravity of 1.05 at 25° C. and a viscosity of about 160,000 cP at 25° C.

EXAMPLE 7

| (i) Oligomer of cyclopentadiene D | 100 parts by weight |
|---|---|
| (ii) Viscosity reducing agent A | 55.6 parts by weight |
| (iii) Dibenzylidenesorbitol | 0.1 part by weight |
| (iv) 1-Methyl-2-pyrrolidone | 0.4 part by weight |
| (v) Finely divided silica A | 5.9 parts by weight |

A composition was prepared in the same manner as in Example 4 except that the above-mentioned components were used. The obtained composition had a specific gravity of 1.05 at 25° C. and a viscosity of about 160,000 cP at 25° C.

EXAMPLE 8

| (i) Oligomer of cyclopentadiene C | 100 parts by weight |
|---|---|
| (ii) Di(2-ethylhexyl) phthalate | 93.20 parts by weight |
| (iii) Dibenzylidenesorbitol | 0.12 part by weight |
| (iv) 1-Methyl-2-pyrrolidone | 0.48 part by weight |
| (v) Finely divided silica A | 6.20 parts by weight |

A composition was prepared in the same manner as in Example 4 except that the above-mentioned components were used. The obtained composition had a specific gravity of 1.05 at 25° C. and a viscosity of about 160,000 cP at 25° C.

Comparative Example 9

| (i) Oligomer of dicyclopentadiene B | 100 parts by weight |
|---|---|
| (ii) Viscosity reducing agent A | 6.20 parts by weight |
| (iii) Dibenzylidenesorbitol | 0.82 part by weight |
| (iv) DMSO | 0.82 part by weight |
| (v) Finely divided silica A | 1.98 parts by weight |

The components (i)–(v) were kneaded at ordinary temperature in a vaccum for 60 minutes to give a composition. The obtained composition had a specific gravity of 1.05 at 25° C. and a viscosity of about 200,000 cP at 25° C.

Evaluation of Performance

The serum or plasma separating compositions obtained in Examples 4 to 8 and Comparative Example 9 were tested for evaluation of performance with respect to the following items.

Blood testing containers were produced from the compositions in the same manner as in the test of the composition of Example 1 and subjected to the following tests.

1) Phase separation test (n=5)

The blood testing container was held on a slope having an angle of inclination of 45° with its opening looking down and allowed to stand at 60° C. for 24 hours. It was then observed whether an oily component is separated from the composition (phase separation).

2) Invertibility test and partition wall stability test (n=5)

The tests were carried out in the same manner as in the tests of the composition of Example 1. It was also observed whether oil drops supposedly owing to the phase separation of the composition exist in a serum phase after centrifugation.

The test results are shown in Table 3.

TABLE 3

| | Phase separation | Invertibility | Oil drops | Partition wall stability |
|---|---|---|---|---|
| Example 4 | Not observed | Good | Not observed | Good |
| Example 5 | Not observed | Good | Not observed | Good |
| Example 6 | Not observed | Good | Not observed | Good |
| Example 7 | Not observed | Good | Not observed | Good |
| Example 8 | Not observed | Good | Not observed | Good |
| Comparative Example 9 | Observed | Good | Observed | Good |

In Table 3, when the oily component was not separated from the composition, the phase separation is indicated as "Not observed". Conversely, when the oily component was separated from the composition, the phase separation is indicated as "Observed". When the composition was positioned between a serum layer and a clot layer to form a partition wall which had thickness of about 7 mm and gave a good separating layer, invertibility is indicated as "Good". Otherwise, the invertibility is indicated as "Poor". When the oil drops were not generated, the oil drops are indicated as "Not observed". Conversely, when the oil drops were generated and a hemolysis test could not be carried out, the oil drops are indicated as "Observed". The partition wall stability is evaluated according to the same criterion as in Table 2.

The thickness of the partition walls formed in the invertibility test was always about 7 mm. In the invertibility test, the compositions of Examples 4 to 8 gave good separating layers, but the composition of Comparative Example 9 gave oil drops.

EXAMPLE 9

| | |
|---|---|
| (i) Oligomer of cyclopentadiene C | 100 parts by weight |
| (ii) Di(2-ethylhexyl) phthalate | 75 parts by weight |
| (iii) Dibenzylidenesorbitol | 0.24 part by weight |
| (iv) Dispersant for organic gelling agent A | 0.24 part by weight |
| (iv) 1-Methyl-2-pyrrolidone | 0.72 part by weight |
| (v) Chlorinated paraffin A | 25 parts by weight |

The component (i) was melted by heating at 130° C. To the resulting melt were added other components, and then the whole was kneaded for 30 minutes to prepare a composition. The composition had a specific gravity of 1.04 at 25° C. and a viscosity of about 120,000 cP.

EXAMPLE 10

| | |
|---|---|
| (i) Oligomer of cyclopentadiene C | 100 parts by weight |
| (ii) Di(2-ethylhexyl) phthalate | 70 parts by weight |
| (iii) Dibenzylidenesorbitol | 0.27 part by weight |
| (iv) Dispersant for organic gelling agent A | 0.27 part by weight |
| (iv) 1-Methyl-2-pyrrolidone | 0.80 part by weight |
| (v) Chlorinated paraffin A | 50 parts by weight |

A composition was prepared in the same manner as in Example 9 except that the above-mentioned components were used. The composition had a specific gravity of 1.05 at 25° C. and a viscosity of about 130,000 cP.

EXAMPLE 11

| | |
|---|---|
| (i) Oligomer of cyclopentadiene C | 100 parts by weight |
| (ii) Di(2-ethylhexyl) phthalate | 50 parts by weight |
| (iii) Dibenzylidenesorbitol | 0.2 part by weight |
| (iv) Dispersant for organic gelling agent A | 0.2 part by weight |
| (iv) 1-Methyl-2-pyrrolidone | 0.6 part by weight |
| (v) Chlorinated paraffin A | 50 parts by weight |

A composition was prepared in the same manner as in Example 9 except that the above-mentioned components were used. The composition had a specific gravity of 1.06 at 25° C. and a viscosity of about 140,000 cP.

EXAMPLE 12

| | |
|---|---|
| (i) Oligomer of cyclopentadiene C | 100 parts by weight |
| (ii) Viscosity reducing agent A | 100 parts by weight |
| (iii) Dibenzylidenesorbitol | 0.24 part by weight |
| (iv) Dispersant for organic gelling agent A | 0.24 part by weight |
| (iv) 1-Methyl-2-pyrrolidone | 0.72 part by weight |
| (v) Chlorinated paraffin B | 10 parts by weight |

A composition was prepared in the same manner as in Example 9 except that the above-mentioned components were used. The composition had a specific gravity of 1.05 at 25° C. and a viscosity of about 120,000 cP.

EXAMPLE 13

| | |
|---|---|
| (i) Oligomer of cyclopentadiene C | 100 parts by weight |
| (ii) Di(2-ethylhexyl) phthalate | 100 parts by weight |
| (iii) Dibenzylidenesorbitol | 0.51 part by weight |
| (iv) 1-Methyl-2-pyrrolidone | 2.02 parts by weight |
| (v) Chlorinated paraffin A | 50 parts by weight |

A composition was prepared in the same manner as in Example 9 except that the above-mentioned components were used. The composition had a specific gravity of 1.04 at 25° C. and a viscosity of about 120,000 cP.

Comparative Example 10

| | |
|---|---|
| (i) Oligomer of dicyclopentadiene B | 100 parts by weight |
| (ii) Viscosity reducing agent A | 6.20 parts by weight |
| (iii) Dibenzylidenesorbitol | 0.82 part by weight |
| (iv) DMSO | 0.82 part by weight |
| (v) Finely divided silica A | 1.98 parts by weight |

The components (i)–(v) were kneaded at ordinary temperature in a vaccum for one hour to prepare a composition. The composition had a specific gravity of 1.05 at 25° C. and a viscosity of about 200,000 cP.

Comparative Example 11

| | |
|---|---|
| (i) Oligomer of cyclopentadiene C | 100 parts by weight |
| (ii) Di(2-ethylhexyl) phthalate | 20 parts by weight |
| (iii) Dibenzylidenesorbitol | 0.07 part by weight |
| (iv) 1-Methyl-2-pyrrolidone | 0.29 part by weight |
| (v) Chlorinated paraffin A | 25 parts by weight |

A composition was prepared in the same manner as in Example 9 except that the above-mentioned components were used. The composition had a specific gravity of 1.07 at 25° C. and a viscosity of about 400,000 cP.

Comparative Example 12

| | |
|---|---|
| (i) Oligomer of cyclopentadiene C | 100 parts by weight |
| (ii) Di(2-ethylhexyl) phthalate | 140 parts by weight |
| (iii) Dibenzylidenesorbitol | 0.13 part by weight |
| (iv) 1-Methyl-2-pyrrolidone | 0.5 part by weight |
| (v) Chlorinated paraffin A | 25 parts by weight |

A composition was prepared in the same manner as in Example 9 except that the above-mentioned components were used. The composition had a specific gravity of 1.02 at 25° C. and a viscosity of about 50,000 cP.

Comparative Example 13

| | |
|---|---|
| (i) Oligomer of cyclopentadiene C | 100 parts by weight |
| (ii) Viscosity reducing agent A | 80 parts by weight |
| (iii) Dibenzylidenesorbitol | 0.24 part by weight |
| (iv) Dispersant for organic gelling agent A | 0.24 part by weight |
| (iv) 1-Methyl-2-pyrrolidone | 0.72 part by weight |
| (v) Chlorinated paraffin B | 0.5 part by weight |

A composition was prepared in the same manner as in Example 9 except that the above-mentioned components were used. The composition had a specific gravity of 1.02 at 25° C. and a viscosity of about 110,000 cP.

Comparative Example 14

| | |
|---|---|
| (i) Oligomer of cyclopentadiene C | 100 parts by weight |
| (ii) Di(2-ethylhexyl) phthalate | 10 parts by weight |
| (iii) Dibenzylidenesorbitol | 0.27 part by weight |
| (iv) Dispersant for organic gelling agent A | 0.27 part by weight |
| (iv) 1-Methyl-2-pyrrolidone | 0.80 part by weight |
| (v) Chlorinated paraffin A | 120 parts by weight |

A composition was prepared in the same manner as in Example 9 except that the above-mentioned components were used. The composition had a specific gravity of 1.11 at 25° C. and a viscosity of about 190,000 cP.

Evaluation of Performance

The serum or plasma separating compositions obtained in Examples 9 to 13 and Comparative Examples 10 to 14 were tested for evaluation of performance with respect to the following items.

Blood testing containers were produced from the compositions in the same manner as in the test of the composition of Example 1 and subjected to the following tests.

1) Phase separation test (n=10)

The test was carried out in the same manner as in the test of the composition of Example 4.

2) Invertibility test and partition wall stability test (n=10)

The tests were carried out in the same manner as in the tests of the composition of Example 4.

3) Radiation irradiation test (n=50)

The test was carried out in the same manner as in the test of the composition of Example 2.

4) Hemolysis test (n=3)

A serum layer was separated from the blood testing container which had been subjected to the tests 2), and hemoglobin (Hb) in the serum was measured. (The analysis was entrusted to Fukuyama Rinsho Clinical Examination Center.)

The test results are shown in Table 4.

TABLE 4

| | Phase separation | Invertibility | Oil drops | Partition wall stability | Bad smell | Hb in serum (mg/dl) |
|---|---|---|---|---|---|---|
| Example 9 | Not observed | Good | Not observed | Good | Not detected | 1 |
| Example 10 | Not observed | Good | Not observed | Good | Not detected | 1 |
| Example 11 | Not observed | Good | Not observed | Good | Not detected | 1 |
| Example 12 | Not observed | Good | Not observed | Good | Not detected | 1 |
| Example 13 | Not observed | Good | Not observed | Good | Not detected | 1 |
| Comparative Example 10 | Observed | Good | Observed | Good | Detected | Not measured |
| Comparative Example 11 | Not observed | Poor | Not observed | Poor | Not detected | Not measured |
| Comparative Example 12 | Not observed | Poor | Not observed | Poor | Not detected | Not measured |
| Comparative Example 13 | Not observed | Poor | Not observed | Poor | Not detected | Not measured |
| Comparative Example 14 | Observed | Poor | Observed | Poor | Not detected | Not measured |

In Table 4, Hb concentration of not lower than 5 mg/dl in serum was regarded as hemolysis in the hemolysis test. The phase separation, invertibility, oil drops and partition wall stability are evaluated according to the same criteria as in Table 3. The bad smell is evaluated according to the same criterion as in Table 1.

EXAMPLE 14

| | |
|---|---|
| (i) Oligomer of cyclopentadiene C | 100 parts by weight |
| (ii) Viscosity reducing agent A | 73 parts by weight |
| (iii) Dibenzylidenesorbitol | 0.1 part by weight |
| (iv) 1-Methyl-2-pyrrolidone | 0.4 part by weight |
| (v) Finely divided silica A | 6.6 parts by weight |
| (vi) Low molecular weight styrene thermoplastic resin | 9.5 parts by weight |

A composition was prepared in the same manner as in Example 9 except that the above-mentioned components were used. The composition had a specific gravity of 1.05 at 25° C. and a viscosity of-about 250,000 cP.

EXAMPLE 15

| | |
|---|---|
| (i) Oligomer of cyclopentadiene C | 100 parts by weight |
| (ii) Viscosity reducing agent A | 67 parts by weight |
| (iii) Dibenzylidenesorbitol | 0.09 part by weight |
| (iv) 1-Methyl-2-pyrrolidone | 0.35 part by weight |
| (v) Finely divided silica A | 6.1 parts by weight |
| (vi) Low molecular weight styrene thermoplastic resin | 0.9 part by weight |

A composition was prepared in the same manner as in Example 9 except that the above-mentioned components were used. The composition had a specific gravity of 1.05 a 25° C. and a viscosity of about 150,000 cP.

Comparative Example 15

| (i) Oligomer of cyclopentadiene C | 100 parts by weight |
|---|---|
| (ii) Viscosity reducing agent A | 67 parts by weight |
| (iii) Dibenzylidenesorbitol | 0.09 part by weight |
| (iv) 1-Methyl-2-pyrrolidone | 0.35 part by weight |
| (v) Finely divided silica A | 6.1 parts by weight |

A composition was prepared in the same manner as in Example 9 except that the above-mentioned components were used. The composition had a specific gravity of 1.05 at 25° C. and a viscosity of about 120,000 cP.

Comparative Example 16

| (i) Oligomer of cyclopentadiene C | 100 parts by weight |
|---|---|
| (ii) Viscosity reducing agent A | 79 parts by weight |
| (iii) Dibenzylidenesorbitol | 0.1 part by weight |
| (iv) 1-Methyl-2-pyrrolidone | 0.4 part by weight |
| (v) Finely divided silica A | 7.2 parts by weight |
| (vi) Low molecular weight styrene thermoplastic resin | 21 parts by weight |

A composition was prepared in the same manner as in Example 9 except that the above-mentioned components were used. The composition had a specific gravity of 1.05 at 25° C. and a viscosity of about 500,000 cP.

Evaluation of performance

The serum or plasma separating compositions obtained in Examples 14 and 15 and Comparative Examples 15 and 16 were tested for evaluation of performance with respect to the following items.

Blood testing containers were produced from the compositions in the same manner as in the test of the composition of Example 1 and subjected to the following tests.

1) Phase separation test (n=10)

The test was carried out in the same manner as in the test of the composition of Example 4.

2) Invertibility test and partition wall stability test (n=10)

The tests were carried out in the same manner as in the tests of the composition of Example 4.

3) Radiation irradiation test (n=50)

The test was carried out in the same manner as in the test of the composition of Example 2.

4) Hemolysis test (n=3)

A serum layer was taken out from the blood testing container which had been subjected to the tests 2), and hemoglobin (Hb) in the serum was measured. (The analysis was entrusted to Fukuyama Rinsho Clinical Examination Center.)

The test results are shown in Table 5.

In Table 5, the performance is evaluated according to the same criteria as in Table 4.

EXAMPLE 16

| (i) Oligomer of cyclopentadiene C | 100 parts by weight |
|---|---|
| (ii) Viscosity reducing agent A | 67 parts by weight |
| (iii) Dibenzylidenesorbitol | 0.09 part by weight |
| (iv) DMA | 0.35 part by weight |
| (v) Finely divided silica A | 6.1 parts by weight |

A composition was prepared in the same manner as in Example 9 except that the above-mentioned components were used. The composition had a specific gravity of 1.05 at 25° C. and a viscosity of about 12,0,000 cP.

EXAMPLE 17

| (i) Oligomer of cyclopentadiene C | 100 parts by weight |
|---|---|
| (ii) Viscosity reducing agent A | 66 parts by weight |
| (iii) Dibenzylidenesorbitol | 0.09 part by weight |
| (iv) DMA | 0.09 part by weight |
| (v) Finely divided silica A | 6.0 parts by weight |

A composition was prepared in the same manner as in Example 9 except that the above-mentioned components were used. The composition had a specific gravity of 1.05 at 25° C. and a viscosity of about 120,000 cP.

EXAMPLE 18

| (i) Oligomer of cyclopentadiene C | 100 parts by weight |
|---|---|
| (ii) Viscosity reducing agent A | 67 parts by weight |
| (iii) Dibenzylidenesorbitol | 0.09 part by weight |
| (iv) DMF | 0.35 part by weight |
| (v) Finely divided silica A | 6.1 parts by weight |

A composition was prepared in the same manner as in Example 9 except that the above-mentioned components were used. The composition had a specific gravity of 1.05 at 25° C. and a viscosity of about 120,000 cP.

Comparative Example 17

| (i) Oligomer of cyclopentadiene C | 100 parts by weight |
|---|---|
| (ii) Viscosity reducing agent A | 66 parts by weight |
| (iii) Dibenzylidenesorbitol | 0.09 part by weight |
| (v) Finely divided silica A | 6.0 parts by weight |

A composition was prepared in the same manner as in Example 9 except that the above-mentioned components

TABLE 5

| | Phase separation | Invertibility | Oil drops | Partition wall stability | Bad smell | Hb in serum (mg/dl) |
|---|---|---|---|---|---|---|
| Example 14 | Not observed | Good | Not observed | Good | Not detected | 1 |
| Example 15 | Not observed | Good | Not observed | Good | Not detected | 1 |
| Comparative Example 15 | Observed | Good | Observed | Good | Not detected | Not measured |
| Comparative Example 16 | Not observed | Poor | Not observed | Poor | Not detected | Not measured | were used. The composition had a specific gravity of 1.05 at 25° C. and a viscosity of about 110,000 cP.

Comparative Example 18

| | |
|---|---|
| (i) Oligomer of cyclopentadiene C | 100 parts by weight |
| (ii) Viscosity reducing agent A | 68 parts by weight |
| (iii) Dibenzylidenesorbitol | 0.09 part by weight |
| (iv) DMA | 0.53 part by weight |
| (v) Finely divided silica A | 6.2 parts by weight |

A composition was prepared in the same manner as in Example 9 except that the above-mentioned components were used. The composition had a specific gravity of 1.05 at 25° C. and a viscosity of about 120,000 cP.

Evaluation of Performance

The serum or plasma separating compositions obtained in Examples 16 to 18 and Comparative Examples 17 and 18 were tested for evaluation of performance with respect to the following items.

Blood testing containers were produced from the compositions in the same manner as in the test of the composition of Example 1 and subjected to the following tests.

1) Phase separation test (n=10)

The test was carried out in the same manner as in the test of the composition of Example 4.

2) Invertibility test and partition wall stability test (n=10)

The tests were carried out in the same manner as in the tests of the composition of Example 4.

3) Radiation irradiation test (n=50)

The test was carried out in the same manner as in the test of the composition of Example 2.

4) Hemolysis test (n=3)

A serum layer was taken out from the blood testing container which had been subjected to the tests 2), and hemoglobin (Hb) in the serum was measured. (The analysis was entrusted to Fukuyama Rinsho Clinical Examination Center.)

The test results are shown in Table 6.

To the component (iv) were added the components (iii) and (v). The components were kneaded under reduced pressure for one hour and dispersed homogeneously to prepare a composition.

The composition had a specific gravity of 1.05 at 25° C. and a viscosity of about 250,000 cP.

Comparative Example 19

A composition was prepared in the same manner as in Example 19 except that the dispersant for the organic gelling agent B was used in place of the dispersant for the organic gelling agent A as the component (iv).

Comparative Example 20

| | |
|---|---|
| (i) Oligomer of dicyclopentadiene A | 100 parts by weight |
| (ii) Viscosity reducing agent A | 7.7 parts by weight |
| (iii) Dibenzylidenesorbitol | 0.1 part by weight |
| (iv) DMSO | 0.4 part by weight |
| (v) Finely divided silica B | 2.3 parts by weight |

The above-mentioned components were kneaded under reduced pressure for one hour to prepare a composition.

Evaluation of performance

The serum or plasma separating compositions obtained in Example 19 and Comparative Examples 19 and 20 were tested for evaluation of performance with respect to the following items.

Blood testing containers were produced from the compositions in the same manner as in the test of the composition of Example 1 and subjected to the following tests.

1) Phase separation test (n=10)

The test was carried out in the same manner as in the test of the composition of Example 4.

TABLE 6

| | Phase separation | Invertibility | Oil drops | Partition wall stability | Bad smell | Hb in serum (mg/dl) |
|---|---|---|---|---|---|---|
| Example 16 | Not observed | Good | Not observed | Good | Not detected | 1 |
| Example 17 | Not observed | Good | Not observed | Good | Not detected | 1 |
| Example 18 | Not observed | Good | Not observed | Good | Not detected | 1 |
| Comparative Example 17 | Not observed | Good | Not observed | Poor | Not detected | 1 |
| Comparative Example 18 | Not observed | Good | Not observed | Good | Not detected | 15 |

In Table 6, the performance is evaluated according to the same criteria as in Table 4.

EXAMPLE 19

| | |
|---|---|
| (iv) Dispersant for organic gelling agent A | 100 parts by weight |
| (iii) Dibenzylidenesorbitol | 25 parts by weight |
| (v) Titanium oxide | 1.5 parts by weight |

2) Invertibility test and partition wall stability test (n=10)

The tests were carried out in the same manner as in the tests of the composition of Example 4.

3) Measurement of biochemical examination value (n=2)

The test was carried out in the same manner as in the test of the composition of Example 1.

The test results are shown in Table 7.

TABLE 7

| | Phase | | | Partition wall | Biochemical examination value (Measured value/Reference value) | | |
|---|---|---|---|---|---|---|---|
| | separation | Invertibility | Oil drops | stability | Item a | Item b | Item c |
| Example 19 | Not observed | Good | Not observed | Good | 0.99 | 0.99 | 1.00 |
| Comparative Example 19 | Not observed | Good | Not observed | Good | 1.67 | 1.90 | 1.62 |
| Comparative Example 20 | Observed | Good | Observed | Poor | 1.25 | 1.35 | 1.18 |

In Table 7, the phase separation, invertibility, oil drops and partition wall stability are evaluated according to the same criteria as in Table 3. The biochemical examination values are evaluated according to the same criterion as in Table 1.

The biochemical measured values of the components in the serum obtained using the composition of Example 19 are equal to those of the reference test in any items. The composition was found to exert no adverse effect on the biochemical examination. The measured values of the components in the serum obtained using the compositions of Comparative Examples 19 and 20 are larger than those of the reference test in any items. The compositions of Comparative Examples 19 and 20 did not give correct measured values.

Since the compositions of the present invention are constituted as above, the compositions exhibit the following effects.

Effects of the First to Sixth Compositions Since the specific polyoxyethylene-polyoxypropyrene block copolymer is used as the dispersant for the organic gelling agent in the first to sixth compositions of the present invention, the organic solvent such as DMSO or DMA is not required. Accordingly, the compositions do not give malodorous substances by irradiation with radiation. In addition, since the dispersant is a hydrophobic high-molecular weight compound, the dispersant also has an advantage of not causing hemolysis, etc. by partially dissolving in blood, serum or plasma.

Effects of the Second Composition

In the second composition, the organic gelling agent is homogeneously dispersed in the oligomer of cyclopentadiene for a short time by the combined action of the polyoxyethylene-polyoxypropyrene block copolymer and the tertiary amine as the dispersant, and thereby preventing both poor invertibility by the rise in thixotropy with the lapse of time and the flow.

Effects of the Third to Sixth Compositions

In the third to sixth compositions, an oligomer of cyclopentadiene having a specific softening point and a specific melting viscosity is used. The oligomer of cyclopentadiene is a solid at ordinary temperature, but the oligomer is apt to flow at ordinary temperature by adding the viscosity reducing agent thereto. The third to sixth compositions obtained by adding the specific organic gelling agent, the specific dispersant, and if necessary, the specific gravity adjusting agent to the oligomer of cyclopentadiene containing the viscosity reducing agent have thixotropy and specific gravity being in suitable ranges for the serum or plasma separating compositions, and substantially do not permit phase separation.

Effects of the Fifth Composition

In the fifth composition, addition of the compatibilizing agent can increase compatibility of the oligomer with the viscosity reducing agent to prevent phase separation almost completely.

Effects of the Sixth Composition

The sixth composition can exhibit a dispersion effect equal to that of the conventional composition in a smaller amount of DMA and/or DMF by using the oligomer of cyclopentadiene having a specific softening point and a specific melting viscosity and the viscosity reducing agent, and adding the organic gelling agent and DMA and/or DMF as the dispersant of the organic gelling agent. As a result, hemolysis is not caused by a decrease in concentration of the dispersant.

Effects of the Seventh Composition

In the seventh composition, since network structure by simple hydrogen bonding of the organic gelling agent exhibits thixotropy, the network structure does not change with the lapse of time unlike the conventional composition. The seventh composition is less susceptible to phase separation.

In the seventh composition, the organic gelling agent mainly participates in imparting thixotropy. Hence, when a little silica is used as the specific gravity adjusting agent, phase separation is not promoted even if the silica agglomerates again.

Since the polyoxyethylene-polyoxypropylene block copolymer is a non-ionic surface-active agent, it disperses the organic gelling agent homogeneously, and exhibits good thixotropy. In addition, since the copolymer has HLB of 1.0 to 9.0 and is far more hydrophobic than general non-ionic surface-active agents, the copolymer is hardly compatible with blood, and thereby exerting no adverse effect on biochemical examination values of blood.

Furthermore, the polyoxyethylene-polyoxypropylene block copolymer has a less temperature-dependent viscosity than the conventional oligomer of cyclopentadiene. Accordingly, the seventh composition is far less temperature-dependent than the conventional composition and is not susceptible to poor separation of serum or plasma in centrifuging at low temperatures, which has so far become an issue.

Industrial Applicability

The present invention relates to serum or plasma separating compositions for use in centrifuging blood utilizing a difference in specific gravity between blood components. The invention provides a serum or plasma separating composition which does not give out a bad smell by sterilization with radiation, has no influence derived from hemolysis, etc. on biochemical examination values of serum or plasma, does not cause phase separation of components, and is equal to the prior art in serum or plasma separating property, preservation stability, etc. Furthermore, the invention provides a serum or plasma separating composition which hardly brings about flow during preservation by standing in a horizontal lying position and hardly exhibits impaired invertibility with the lapse of time.

We claim:

1. A serum or plasma separating composition comprising an oligomer of cyclopentadiene, an organic gelling agent and a dispersant for the organic gelling agent, the organic gelling agent comprising a condensation product of sorbitol and an aromatic aldehyde, the dispersant for the organic gelling agent comprising a polyoxyethylene-polyoxypropylene block copolymer having HLB of 1.0 to 9.0, the composition comprising 0.02 to 3 parts by weight of the organic gelling agent, and 0.1 to 15 parts by weight of the dispersant for the organic gelling agent per 100 parts by weight of the oligomer of cyclopentadiene.

2. A serum or plasma separating composition comprising an oligomer of cyclopentadiene, an organic gelling agent and a dispersant for the organic gelling agent, the organic gelling agent comprising a condensation product of sorbitol and an aromatic aldehyde, the dispersant for the organic gelling agent comprising a polyoxyethylene-polyoxypropylene block copolymer having HLB of 1.0 to 9.0, and a tertiary amine compound having two methyl groups and an alkyl group having not less than 10 carbon atoms, the composition comprising 0.03 to 0.5 parts by weight of the tertiary amine compound, 0.02 to 3 parts by weight of the organic gelling agent, and 0.1 to 15 parts by weight of the polyoxyethylene-polyoxypropylene block copolymer per 100 parts by weight of the oligomer of cyclopentadiene.

3. A serum or plasma separating composition comprising an oligomer of cyclopentadiene, a viscosity reducing agent, an organic gelling agent and a dispersant for the organic gelling agent, the oligomer of cyclopentadiene having a softening point of 70° to 140° C. and a melting viscosity of 30 to 500 centipoises at 180° C., the viscosity reducing agent comprising a phthalate ester, the organic gelling agent comprising a condensation product of sorbitol and an aromatic aldehyde, the dispersant for the organic gelling agent being selected from the group consisting of a polyoxyethylene-polyoxypropylene block copolymer having HLB of 1.0 to 9.0, 1-methyl-2-pyrrolidone and a mixture thereof, the composition comprising 0.02 to 3 parts by weight of the organic gelling agent, 0.1 to 15 parts by weight of the dispersant for the organic gelling agent, and 30 to 130 parts by weight of the viscosity reducing agent per 100 parts by weight of the oligomer of cyclopentadiene.

4. A serum or plasma separating composition comprising an oligomer of cyclopentadiene, a viscosity reducing agent, an organic gelling agent, a dispersant for the organic gelling agent and a specific gravity adjusting agent, the oligomer of cyclopentadiene having a softening point of 70° to 140° C. and a melting viscosity of 30 to 500 centipoises at 180° C., the viscosity reducing agent comprising a phthalate ester, the organic gelling agent comprising a condensation product of sorbitol and an aromatic aldehyde, the dispersant for the organic gelling agent being selected from the group consisting of a polyoxyethylene-polyoxypropylene block copolymer having HLB of 1.0 to 9.0, 1-methyl-2-pyrrolidone and a mixture thereof, the specific gravity adjusting agent comprising chlorinated paraffin, the composition comprising 30–130 parts by weight of the viscosity reducing agent, 0.02 to 3 parts by weight of the organic gelling agent, 0.1 to 15 parts by weight of the dispersant for the organic gelling agent per 100 parts by weight of the oligomer of cyclopentadiene, and 1 to 100 parts by weight of the specific gravity adjusting agent per 100 parts by weight of the oligomer of cyclopentadiene.

5. A serum or plasma separating composition comprising an oligomer of cyclopentadiene, a compatibilizing agent, a viscosity reducing agent, an organic gelling agent and a dispersant for the organic gelling agent, the oligomer of cyclopentadiene having a softening point of 70° to 140° C. and a melting viscosity of 30 to 500 centipoises at 180° C., the compatibilizing agent comprising a styrene thermoplastic resin having a low molecular weight, the viscosity reducing agent comprising a phthalate ester, the organic gelling agent comprising a condensation product of sorbitol and an aromatic aldehyde, the dispersant for the organic gelling agent being selected from the group consisting of a polyoxyethylene-polyoxypropylene block copolymer having HLB of 1.0 to 9.0, 1-methyl-2-pyrrolidone and a mixture thereof, the composition comprising 0.1 to 15 parts by weight of the compatibilizing agent, 0.02 to 3 parts by weight of the organic gelling agent, 0.1 to 15 parts by weight of the dispersant for the organic gelling agent, and 30 to 130 parts by weight of the viscosity reducing agent, per 100 parts by weight of the oligomer of cyclopentadiene.

6. A composition as defined in any one of claims 3, 4, or 5 wherein the dispersant is 1-methyl-2-pyrrolidone present in an amount of 0.05 to 5 parts by weight per 100 parts by weight of the oligomer of cyclopentadiene.

7. A serum or plasma separating composition comprising an oligomer of cyclopentadiene, a viscosity reducing agent, an organic gelling agent and a dispersant for the organic gelling agent, the oligomer of cyclopentadiene having a softening point of 70° to 140° C. and a melting viscosity of 30 to 500 centipoises at 180° C., the viscosity reducing agent comprising a phthalate ester, the organic gelling agent comprising a condensation product of sorbitol and an aromatic aldehyde, the dispersant for the organic gelling agent being selected from the group consisting of N,N-dimethylacetamide, N,N-dimethylformamide and a mixture thereof, the composition comprising 0.01 to 15 parts by weight of the dispersant for the organic gelling agent, 0.02 to 3 parts by weight of the organic gelling agent, and 30 to 130 parts by weight of the viscosity reducing agent, per 100 parts by weight of the oligomer of cyclopentadiene.

8. A composition as defined in any one of claims 3, 4, 5, or 7 wherein the dispersant is a polyoxyethylene-polyoxypropylene block copolymer present in an amount of 0.1 to 15 parts by weight per 100 parts by weight of the oligomer of cyclopentadiene.

9. A composition as defined in any one of claims 1, 2, 3, 4, 5, or 7 which further comprises up to 50 parts by weight of a specific gravity adjusting agent per 100 parts by weight of the oligomer of cyclopentadiene.

10. A composition as defined in any one of claims 1, 2, 3, 4, 5, or 7 which further comprises up to 50 parts by weight of a viscosity reducing agent per 100 parts by weight of the oligomer of cyclopentadiene.

11. A serum or plasma separating composition comprising a base resin and an organic gelling agent, the base resin comprising a polyoxyethylene-polyoxypropylene block copolymer having HLB of 1.0 to 9.0, the organic gelling agent comprising a condensation product of sorbitol and an aromatic aldehyde, wherein the amount of organic gelling agent is 5 to 100 parts by weight per 100 parts by weight of the polyoxyethylene-polyoxypropylene block copolymer.

12. A composition as defined in claim 11 which further comprises up to 40 parts by weight of a specific gravity adjusting agent per 100 parts by weight of the polyoxyethylene-polyoxypropylene block copolymer.

13. A composition as defined in claim 11 which further comprises up to 40 parts by weight of a viscosity reducing agent per 100 parts by weight of the polyoxyethylene-polyoxypropylene block copolymer.

14. A composition as defined in any one of claims 1, 2, 3, 4, 5, 7, or 11 which has a specific gravity of 1.03 to 1.08 at 250° C.

15. A composition as defined in any one of claims 1, 2, 3, 4, 5, 7, or 11 which has a viscosity of 50.000 to 1.000.000 centipoises at 25° C.

16. A composition as defined in claim 7 wherein the composition comprises 0.01 to 0.4 parts by weight of the dispersant for the organic gelling agent per 100 parts by weight of the oligomer of cyclopentadiene.

* * * * *